United States Patent [19]

Marino, Jr. et al.

[11] 4,431,009
[45] Feb. 14, 1984

[54] APPARATUS FOR MEASURING BLOOD PRESSURE

[75] Inventors: Joseph A. Marino, Jr.; Matthew E. Bellin, both of Minneapolis, Minn.

[73] Assignee: Biomedical Dynamics Corporation, Minneapolis, Minn.

[21] Appl. No.: 299,671

[22] Filed: Sep. 8, 1981

[51] Int. Cl.³ ............................................. A61B 5/02
[52] U.S. Cl. .................................. 128/673; 128/674; 128/675
[58] Field of Search ................. 73/707; 128/1 D, 673, 128/674, 675; 251/122, DIG. 4

[56] References Cited

U.S. PATENT DOCUMENTS

| | | | |
|---|---|---|---|
| 1,121,105 | 12/1914 | Karlson | 73/707 |
| 1,905,782 | 4/1933 | Amdursky | 73/707 |
| 2,064,268 | 12/1936 | Parker | 73/707 |
| 2,600,324 | 6/1952 | Rappaport | 73/388 |
| 2,841,984 | 7/1958 | Green | 73/707 |
| 3,122,136 | 2/1964 | Murphy, Jr. | 128/673 |
| 3,157,201 | 11/1964 | Littmann | 128/675 |
| 3,769,964 | 11/1973 | Smith | 128/672 |
| 3,865,100 | 2/1975 | Kanai et al. | 73/707 |
| 4,072,146 | 2/1978 | Howes | 128/2.05 |
| 4,206,761 | 6/1980 | Cosman | 128/660 |
| 4,227,420 | 10/1980 | Lamadrid | 128/675 |
| 4,269,387 | 5/1981 | Reynolds et al. | 251/DIG. 4 |
| 4,311,170 | 1/1982 | Dolan | 251/122 |
| 4,335,729 | 6/1982 | Reynolds et al. | 128/674 |

OTHER PUBLICATIONS

"Continuous Flushing Systems" by Latimer in Anesthesia, 1974, vol. 29, pp. 307-317.
Article entitled "Long-Term Clinical Recording of Static and Dynamic Intra-Arterial Blood Pressure" by Magnes & Nornes, Acta Anaesth, Scand. 1974, 325-223.
Direct and Indirect Measurement of Blood Pressure by Geddes, Chapter 1, pp. 9 through 69.
Book entitled "Cardiovascular Fluid Dynamics" by Bergel from Academic Press 1972, Chap. 2, at pp. 11 through 50.
Instructions for the Accunamic Brand Damping Device, Cat. No. ACN-01 of Sorenson Research Company.

Primary Examiner—Kyle L. Howell
Assistant Examiner—George Yanulis
Attorney, Agent, or Firm—Kinney, Lange, Braddock, Westman and Fairbairn

[57] ABSTRACT

The open end of a catheter is inserted in the blood vessel of a patient. The catheter is connected by hollow tubing to a physiologic pressure transducer. The tube is filled with an intermediate pressure-transmitting fluid such as a physiologic saline solution. An infusion device between the patient and the transducer constantly flushes the system with a slow flow of fluid. Blood pressure variations are transmitted through the fluid to the transducer, which converts the pressure to electronic information and transmits the information to a monitor for display. Between the infusion device and the transducer is a variable restrictor which damps the pressure waves in the fluid. This restrictor is used to tune the system to eliminate resonant waves, which distort the monitoring reading. In one form, the variable restrictor includes a valve having an orifice, the effective size of which is reduced or enlarged by compressing and releasing a deformable, flexible ring. In another form, the variable restrictor includes a valve which has a valve seat with a flow opening through which the fluid pressure wave passes. To control pressure wave flow through the valve, a valve needle is moved toward and away from a valve seat, which reduces and increases the size of the flow opening.

13 Claims, 8 Drawing Figures

APPARATUS FOR MEASURING BLOOD PRESSURE

BACKGROUND OF THE INVENTION

1. Field of the Invention

The present invention relates to catheter type blood pressure measuring devices, which use transducers to develop signals responsive to fluid pressure waves present in blood vessels in which the catheters are inserted; and presents an apparatus for damping out resonant pressure waves from the pressure waves truly representative of the blood pressure in the vessel.

2. Description of the Prior Art

It is well known in the prior art that blood pressure can be measured by means of a catheter inserted in a patient's vessel. See, for example, U.S. Pat. No. 2,600,324 to Rappaport issued June 10, 1952 and U.S. Pat. No. 3,122,136 to Murphy issued Feb. 25, 1964.

The damping of pulses in fluid is also known in the prior art. An example of damping is shown in U.S. Pat. No. 2,064,268 to Parker issued Dec. 15, 1936, in which movable rods in a pair of cylinders are used to absorb some of the fluid pressure. This device was not related to sterile medical applications, but does show one method of damping of fluid pressure.

It is known in the prior art that reducing the size of the opening through which fluid waves move will reduce net pressure. In patents, such as U.S. Pat. No. 1,121,105 to Karlson issued Dec. 15, 1914, this method was used to prevent surges of pressure from breaking the old-fashioned reading devices.

It is known that resonant waves can reduce the accuracy of the reading of blood pressure in catheter-type measuring devices. U.S. Pat. No. 3,865,100 to Kanai et al issued Feb. 11, 1975 attempted to solve this through a resilient damping device attached to a transducer which absorbs some of the pressure. This Kanai et al patent teaches no method of adjusting the rate of damping.

The following patents were found in a search of an early form of the invention; but do not seem particularly relevant to the present invention:

| U.S. PAT. DOCUMENTS | | |
| --- | --- | --- |
| U.S. PAT. NO. | INVENTOR | ISSUE DATE |
| 1,905,782 | Amdursky | April 25, 1933 |
| 2,841,984 | Green | July 8, 1958 |
| 3,157,201 | Littmann | November 17, 1973 |
| 3,769,964 | Smith | March 6, 1973 |
| 4,072,146 | Howes | February 7, 1978 |
| 4,206,761 | Cosman | June 10, 1980 |

The following four publications discuss methods of correcting blood pressure measurement. An article entitled "Continuous Flushing Systems" by R. D. Latimer and K. E. Latimer in "Anesthesia", 1974, Volume 29, pages 307–317, discusses adding inertive resistance to the catheter system, but primarily focuses on parallel damping. It does not teach series damping by restriction.

An article entitled "Long-Term Clinical Recording of Static and Dynamic Intra-Arterial Blood Pressure" by B. Magnes and H. Nornes, Acta anaesth, Scand. 1974, 18, 215–223, discusses the use of a screw clamp to compress the infusion tubing. This article does not address the problem of resonant waves, however. This refers to the outdated problem of increased compliance in the monitoring system introduced by what are now-obsolete infusion machines. This screw clamp method isolated the infusion machine from the monitoring system and thus eliminated the extra compliance which it introduced. The problem addressed by the present invention is that of too little compliance or too little friction, which is the opposite of what is taught by this reference.

A book by L. A. Geddes entitled "The Direct and Indirect Measurement of Blood Pressure" discusses in Chapter 1, pages 9 through 69, the relation between the length of a needle for blood pressure and the damping coefficient. This article in general discussed the proper damping coefficient to be achieved by a system for measuring blood pressure. This article arrived at 0.7 as a theoretical damping coefficient needed to obtain critical damping. After this article, it has been found in practical experiments that 0.64 is the optimum practical value.

In a book entitled "Cardiovascular Fluid Dynamics" by D. H. Bergel from Academic Press 1972, Chapter 2 by I. T. Gabe at pages 11 through 50, includes an early discussion of damping waves in blood pressure measuring devices. This article discusses an older technology, such as placing a damping resistance at the open end of the catheter. This is unsatisfactory in that it is within the patient and inaccessible to external adjustment. The article also mentions the possibility of varying damping resistance with a needle valve. No apparatus for accomplishing this is known. The prior art encountered the problem of damping devices preventing flushing of the catheter. If the apparatus is not constantly flushed, blood will clot in it and block the system. This long-felt problem was not resolved in the prior art. After this mentioned of series damping by restriction, the article goes on to discuss parallel damping, which is the method followed by the industry every since. Parallel damping involves adding resistance and compliance to the measuring system out of line with the flow of pressure waves. Parallel damping is inferior to damping in series for two reasons. First, parallel damping often uses an air cushion to absorb pressure. This air may escape into the system. Air in the system can distort pressure readings and can also harm or kill the patient if it escapes into a blood vessel. Second, the amount of damping effect achievable is less with a parallel system. The more severe cases of resonance cannot be controlled as effectively by a parallel device.

No apparatus has been found in the prior art which provides variable series damping. No such apparatus has solved the problem of interference with constant flushing of the system.

SUMMARY OF THE INVENTION

The present invention is related to damping resonant pressure waves in a catheter type apparatus for measuring blood pressure. The open end of a catheter is inserted in a blood vessel of a patient. The other end of the catheter is fitted with a conduit such as hollow plastic tubing which leads to the measuring apparatus. The conduit is filled with a fluid for transmitting pressure, such as a physiologic saline solution. The fluid contacts the blood and variations in blood pressure are transmitted through the fluid. Blood pressure is measured by a pressure transducer which senses pressure waves in the fluid and converts them to electrical signals to be displayed on a monitor.

The accuracy of the blood pressure reading is affected by resonant waves in the fluid. Resonant waves result when pressure waves echo off of the transducing means and reverberate through the apparatus. These waves return to the patient and back to the transducing means. On their return to the transducing means the resonant waves are measured as if they represent blood pressure. This distorts the wave form presented on the monitoring device and degrades the accuracy of the system.

The present invention damps these resonant waves by variably restricting flow of the waves. Preferably an infusion device continually adds saline solution to keep the apparatus clear of blood. A variable restrictor means is connected in the apparatus, preferably between the infusion device and the pressure-transducing means. In a preferred embodiment, control of flow through the body of a variable restrictor is accomplished by compressing a deformable ring which controls the effective size of the central orifice of the ring.

Another preferred embodiment includes a valve in which a valve needle is moved in relation to a valve seat, regulating and controlling the pressure wave. In this form of the invention as shown, the valve allows pressure wave transference and flow in a generally direct path. A valve seat in a passage in a valve body is shaped like a conical frustrum. The seat sits at an acute angle to the passage. A valve needle opening enters the valve body at an angle so that it is aligned with the seat. The valve needle has a face which is shaped to conform to and seal against the seat, regulating and controlling the movement of pressure waves through the fluid in the passage.

The apparatus of the present invention can be tuned by an operator to achieve a more accurate blood pressure reading, eliminating the resonant waves.

DETAILED DESCRIPTION OF THE PREFERRED EMBODIMENTS

Figure 1:
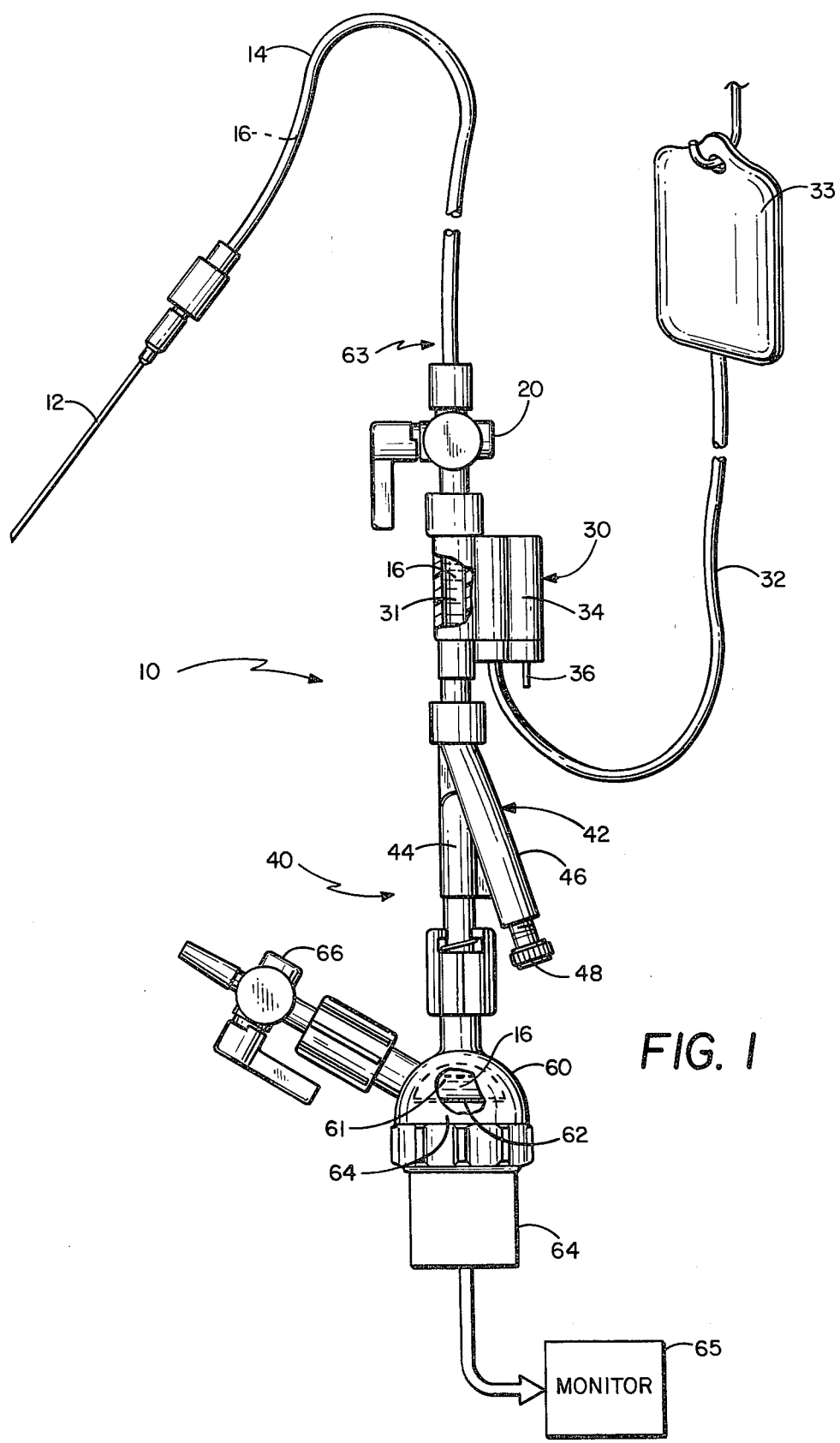
FIG. 1 is a side elevational view of a first form of an apparatus for measuring blood pressure, an information display monitor being schematically represented.

A first form of apparatus for measuring blood pressure 10 as seen in FIG. 1 includes a catheter 12 adapted to be inserted into a blood vessel of a patient whose blood pressure is to be monitored. The catheter can be of any usual or preferred design and construction. Attached and open to the catheter 12 is a conduit or hollow flexible plastic tubing 14. Conduit 14 and catheter 12 are filled with an intermediate pressure transmitting fluid 16, which is usually a physiologic saline solution. Pressure changes in the blood are transmitted through this fluid which is in constant contact with the blood. A stopcock 20 is connected in the conduit 14 so that the catheter may be closed off from the rest of the apparatus. These parts are sterile and disposable to satisfy hospital standards.

If blood is allowed to persist in catheter 12, it can clot and block the apparatus. Therefore, a constant flow of intermediate fluid 16 must be maintained through the apparatus. Connected to hollow tubing 14 is an infusion device 30. Such devices are well known in the art. Infusion device 30 can be of any usual or preferred design or construction. For example, a Pharmaseal brand continuous flush device may be used.

An infusion passage 31 is provided in infusion device 30 for flow of fluid 16 into catheter 12 and the body of the patient. An infusion tube 32 leads to a fluid reservoir or bag 33 containing a reservoir of pressure transmitting fluid 16. Infusion device 30 slowly adds this intermediate fluid 16 to conduit 14. This slow flow isolates the fluid reservoir from the measuring apparatus 10 so that it does not affect pressure readings. This flow moves through conduit 14 and catheter 12, keeping them clear of blood. Inside infusion device 30 has a fast flush valve 34. A snap handle 36 is attached to the fast flush valve 34. Valve 34 and handle 36 are made of soft resilient material, like rubber, for instance.

Before catheter 12 is inserted in the blood vessel of the patient, the conduit 14 and catheter 12 are cleared of air by pulling on handle 36 and releasing it. This opens valve 34 and allows a quick rush of fluid 16 through the conduit and catheter. This fills the system with fluid and eliminates air bubbles which could harm or kill the patient if allowed in the bloodstream.

A variable restrictor means 40 constructed according to the present invention is open to the infusion passage 31 of the infusion device 30 on the opposite end of infusion passage from the catheter 12. The connection between the infusion passage 31 and variable restrictor means 40 is a continuation of conduit 14.

Figure 2:
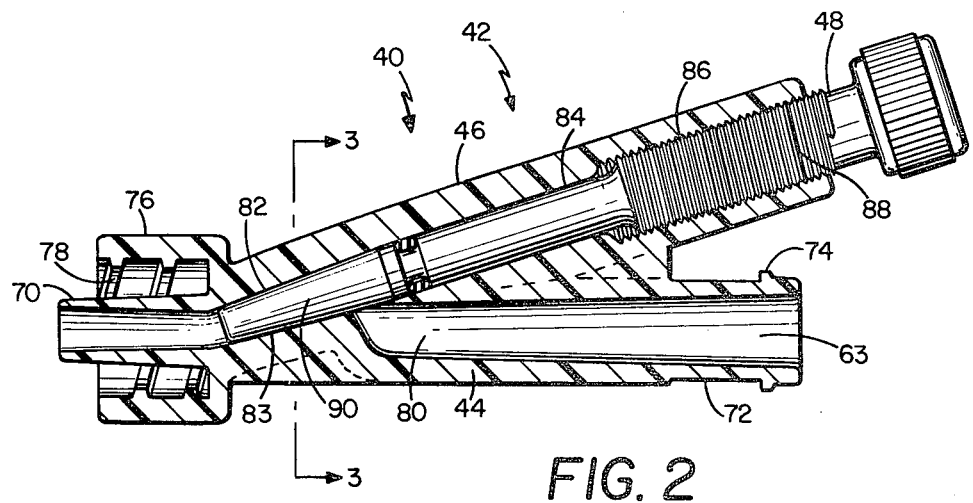
FIG. 2 is a longitudinal cross sectional view of a variable restrictor as seen in FIG. 1.
Figure 3:
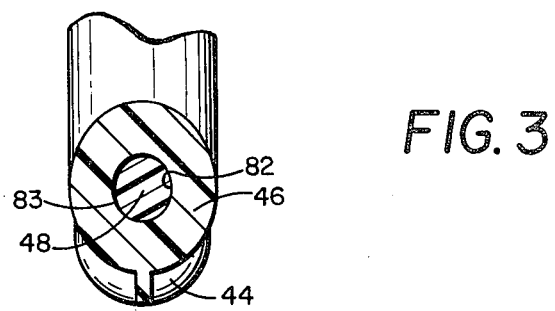
FIG. 3 is a cross sectional view taken on line 3—3 of FIG. 2.

In the first form of the invention as seen in FIGS. 1, 2 and 3, the variable restrictor means 40 is constituted as a needle valve 42 which comprises a valve body 44, valve needle guide 46 and a valve needle 48. Needle valve 42 is adjustable to control movement of pressure waves in the fluid. Because variable restrictor means 40 (needle valve 42) is preferably not between infusion device 30 and the patient, it does not interfere with the flow of fluid needed to keep the apparatus clear of blood. A continuous, steady, and slow flow from infusion device 30 will not affect the damping or measurement procedures.

Next in the sequence away from the patient is a transducer dome 60 which is filled with intermediate fluid 16, as is the rest of the disposable portion of the apparatus. Transducer dome 60 defines a dome-shaped chamber 61 with a pressure transmitting diaphragm 62 against which pressure in fluid 16 acts. Conduit 14, infusion passage 31, variable restrictor means 40, and chamber 61 together form a duct 63 which is filled with fluid 16 for transmitting pressure waves from the blood vessel to diaphragm 62. Attached to transducer dome 60 is physiologic pressure transducer 64. Transducer 64 contacts pressure transmitting diaphragm 62. Variations in pressure against pressure transmitting diaphragm 62 are received by transducer 64 and changed to electrical signals for display. Transducer 64 can be of any usual or preferred construction. A variety of such transducers are well known in the art. For example, a Statham brand transducer employs wire strain gauge. Pressure acting on the transducer deforms a wire. This varies the electrical resistance of the wire. The change in resistance is then displayed on a monitor as an indicator of blood pressure. Solid state models can also be used.

Transducers 64 are relatively expensive devices and are reused. Everything else in the apparatus is made of disposable materials such as plastic, so that fresh sterile apparatus is used for each patient. Pressure transmitting diaphragm 62 isolates the sterile fluid 16 and the disposable parts of apparatus 10 from the reusable transducer 64. Transducer 64 is electrically connected to a monitor 65, which is shown schematically in FIG. 1. Monitor 65 displays the blood pressure wave forms which represent blood pressure plotted against time.

Any air bubbles in the measuring apparatus will distort the blood pressure reading, so they must be eliminated prior to insertion of the catheter in a patient's blood vessel. Attached to transducer dome 60 and open to chamber 61 is a relief valve 66. To clear air bubbles out of the variable restrictor means 40 and the transducer dome 60, stopcock 20 is shut to isolate the portion of the apparatus 10 on the transducer side of stopcock 20 away from the catheter. Relief valve 66 is opened. Snap handle 36 is pulled and released allowing a surge of fluid 16 to flow through infusion device 30, through the variable restrictor means 40, through transducer dome 60 and out relief valve 66. This flow is continued until a bubble-free intermediate fluid 16 throughout duct 63 is assured.

The apparatus 10 operates by transmitting pressure waves representative of the pressure in the catheterized blood vessle through fluid 16 in duct 63. The pressure waves act against pressure transmitting diaphragm 62 and are sensed by transducer 64. Transducer 64 converts the physical forces of the pressure waves to electronic signals which are displayed as wave forms on the monitor 65. The pressure due to the constant slow flow of fluid 16 added by infusion device 30 is negligible.

FIG. 2 shows needle valve 42 and the detail of a Luer connector. These or similar connectors can be used to interconnect the various elements of the apparatus. Male end 70 of a Luer connector on the needle valve 42 is inserted into a female end of the infusion device 30 (not shown). The female end of the infusion device is identical to female end 72 of the needle valve 42. Each female end 72 includes a flange 74. A housing 76 around male end 70 has internal threads 78. After male end 70 is inserted into female end 72, the apparatus is rotated clockwise so that the flange of the female end of the infusion device corresponding to flange 74 engages threads 78, locking the male end against the female end. In some embodiments of Luer connectors, housing 76 is free to rotate on the male end 70. This allows locking of the male and female ends without requiring that the entire apparatus to which the Luer connector is attached be rotated.

Passing longitudinally through the body 44 of needle valve 42 is generally straight passage 80, unlike medical valves in the prior art which employ passages including sharp angles. A sharp change in direction in the line of pressure wave transmission may distort pressure readings, make flushing difficult and trap air bubbles. In contrast, this valve 42 allows the direct, in-line, transmission of the fluid pressure wave from passage 31 of infusion device 30 to diaphragm 62 through intermediate fluid 16. It will be noted that the passage through the ends 70 and 72 are aligned with each other. This design also allows the valve body 44, including valve needle guide 46, to be injection molded in plastic in one piece. This greatly reduces cost of production and the chance of leakage at a connection or weld.

Located in passage 80 of valve 42 on an acute angle to the axis of passage 80 is an elongated, conical valve seat 82, which provides an orifice 83 through which pressure waves pass. The valve needle guide 46 extends away from body 44 of valve 42 at the same angle to body 44 as the valve seat 82 extends away from passage 80.

Vavle needle 48 extends into a valve needle opening 84 through valve needle guide 46. Internal threads 86 on valve needle opening 84 mate with external threads 88 on valve needle 48. As valve needle 48 is rotated clockwise it is moved by threads 88 and 86 into valve needle opening 84. A conical valve needle face 90 of valve needle 48 mates with conical valve seat 82 as needle 48 moves toward seat 82. This controls and restricts the passing of the pressure waves in fluid 16 through orifice 83 in valve seat 82. Since the face 90 of valve needle 48 is a conical frustum, the effective area of orifice 83 is enlarged as face 90 moves away from valve seat 82.

In FIG. 3, the oval cross sectional shape of valve seat 82 indicates that the valve seat extends away from the passage 80 at an angle.

Figure 4:
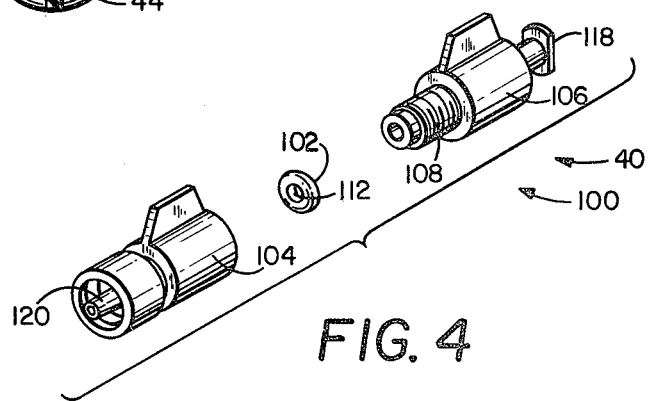
FIG. 4 is an exploded view of an alternate embodiment of variable restrictor useful in a second form of such apparatus.
Figure 5:
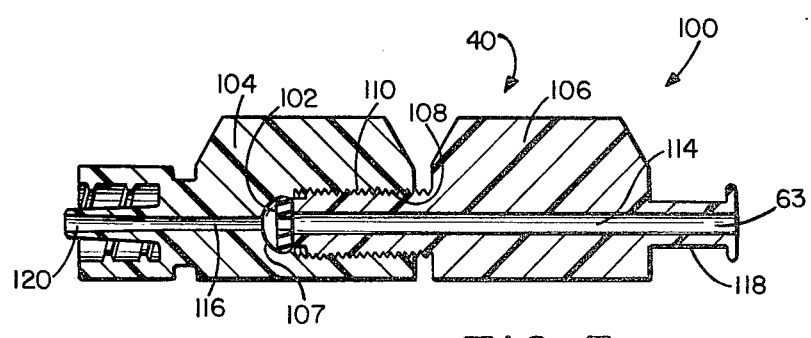
FIG. 5 is an enlarged longitudinal cross sectional view of the variable restrictor of FIG. 4.

An alternate embodiment of variable restrictor means 40 useful in connection with a second form of the invention is shown in FIGS. 4 and 5. In this embodiment, a restrictor valve 100 controls passing of the pressure waves in intermediate fluid 16 from the infusion passage 31 to diaphragm 62 by controlling the size of a central opening or orifice 112 through an O-ring 102. O-ring 102 is made of a compressable deformable material such as rubber. Restrictor valve 100 includes a valve body 104 and a valve element 106. Valve element 106 has external threads 108 which engage internal threads 110 in the valve body 104. Valve body 104 has a basin-shaped valve seat 107 which receiveds O-ring 102. As element 106 is rotated clockwise, O-ring 102 is squeezed against valve seat 107. The central opening or orifice 112 of O-ring 102 becomes progressively smaller as the O-ring is squeezed between valve element 106 and valve seat 107. Element 106 has a passage 114 therethrough which aligns with a passage 116 through body 104 to transmit pressure waves carried by pressure transmitting fluid 16.

Luer fittings are used to connect restrictor valve 100 into the rest of the apparatus 10. As shown, valve elemtn 106 has a female Luer fitting 118 and valve body 104 has a male Luer fitting 120, for connection into conduit 14 to form part of duct 63.

Each form of variable restrictor means 40 is delivered in a sealed sterile package, as are other disposable parts in blood pressure measuring apparatus 10. As shown, the other components are standard hospital items.

Figure 8:
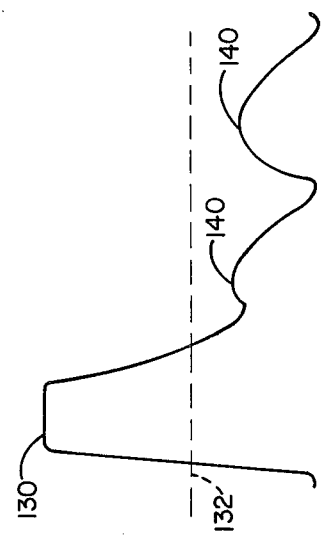
FIG. 8 is a representation of a wave form occuring when the apparatus is over-damped.
Figure 7:
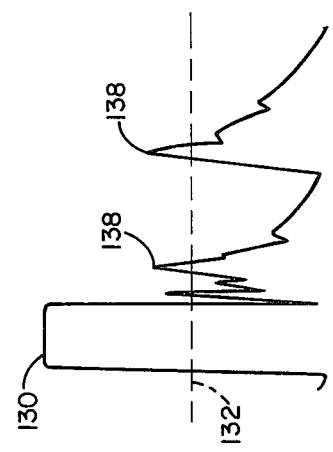
FIG. 7 is a representation of a similar wave form but occuring when resonant waves are present in the apparatus.
Figure 6:
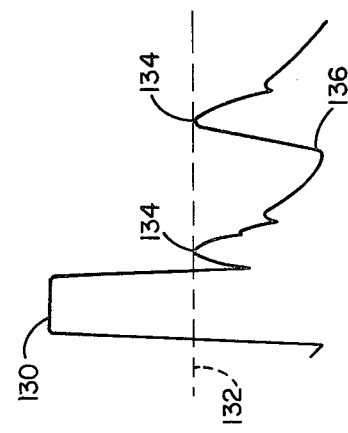
FIG. 6 is a representation of a pressure/time wave form such as displayed on the monitor of a properly damped apparatus of the invention.

The variable restrictor means 40 of either form of the invention is attached in the pressure line of conduit 14 by Luer fittings, in relative position as shown in FIG. 1. Air is purged from all components as discussed above. The catheter is then inserted in the blood vessel. The transducer means 64 is activated to show pressure waves on the monitor. The variable restrictor means 40 must then be adjusted. This is done by executing a square wave or "snap" test. FIGS. 6 through 8 are examples of wave-forms portrayed on display monitor 65. The display is in the form of a graph, with the vertical axis representing amplitude of the pressure waves and the horizontal axis representing time. In FIG. 6, the peaks 134 of the wave forms represent the systolic blood pressure and the valleys 136 represent diastolic blood pressure. Dotted line 132 represents an arbitrary amplitude of the systolic blood pressure of a typical patient. The wave forms must be analyzed by a skilled operator who tunes the system. This interpretation is a somewhat subjective evaluation of the curves well known in the art. Similar wave form evaluations are done in the use of other types of unrelated damping devices. For instance, the instructions for the Accunamic brand damping device, Cat. No. ACM-01 of the Sorenson Research Company employ such analysis.

The fast flush valve 34 of infusion device 30 is actuated by pulling snap handle 36 and holding it out for a second. This injects a surge of fluid in the apparatus which increases pressure and drives the monitor trace to the top of the monitor scope as shown by the flat top or square line 130 in FIGS. 6 through 8. Snap handle 36 is then released with a "snap". Fast flush valve 34 closes with a "snap", and the pressure drops and settles to wave form, as shown in FIG. 6, for example. The systolic peaks are recorded at the correct vertical position along line 132 because FIG. 6 represents the display on a monitor of a properly damped blood pressure measuring apparatus.

FIG. 7 shows a poor square wave test. The system here is underdamped. The trace on the monitor overshoots the proper blood pressure wave form parameter 132 and resonates several times before showing a steady wave. Here, systolic peaks 138 exceed the proper magnitude indicated by dotted line 132. This is because resonant waves are added to blood pressure waves to compose a pressure reading higher than true blood pressure. This is corrected by adjusting the variable restrictor means to restrict movement of pressure waves.

For instance, in the first form of the invention as illustrated in FIGS. 1 through 3, valve needle 48 is turned clockwise to insert face 90 further into valve seat 82. This reduces the effective size of orifice 83, which reduces and damps the resonant waves.

The restrictor valve 100 in the second form of the invention is tightened by turning valve element 106 clockwise, which reduces the effective area of central opening 112 of O-ring 102.

An overdamped system is shown in FIG. 8. The trace shows a sluggish square wave test with poor wave form reproduction. Systolic peaks 140 of FIG. 8 never reach the true blood pressure reading, indicated by line 132. This could be caused by an improperly adjusted variable restrictor means which is too restrictive, or by air bubbles, blood, or a kink in the monitoring line. The system should be checked to make sure that air and blood are flushed out of the system. If the overdamped square wave test pattern still shows, the variable restrictor means should be loosened by turning valve needle 48 (first form) or valve element 106 (second form) counterclockwise to allow less restriction to the pressure wave.

The ideal square wave test should result in a wave form which looks like FIG. 6. As in the prior art, the trained operator recognizes that the systolic peaks 134 are of the proper height and that the wave leading to valleys 136 is of the proper shape.

Either of the variable restrictor means 40 can be adjusted to properly damp the blood pressure measuring apparatus 10, no matter what combination of catheter, tubing, stopcocks, infusion device, transducer dome or transducer is used. Different transducers 64 have different response, but there is no need to identically match all of the apparatus in the system. One need merely adjust the variable restrictor means 40 to show a proper square wave test. This apparatus allows the operator to damp accurately in-line with the operating system. The disadvantages of dealing with a parallel damping device are avoided. The system also allows the catheter to be continually flushed out with the intermediate pressure transmitting fluid without interference from the damping device.

Although the present invention has been described with reference to preferred embodiments, workers skilled in the art will recognize that changes may be made in form and detail without departing from the spirit and scope of the invention. Workers skilled in the art will also recognize that embodiments of the invention may be incorporated as an integral part of other components in the monitoring system such as the infusion device, transducer dome, or stop cock.

What is claimed is:

1. An apparatus for measuring blood pressure comprising:
    an open-ended catheter having a first end adapted to be inserted into a blood vessel;
    pressure transducing means including a fluid chamber, said pressure transducing means being adapted to develop a useful signal responsive to pressure variations in the fluid chamber;
    a duct providing a fluid passageway open between a second end of said catheter and said transducing means fluid chamber;
    adjustable restrictor means in series with said catheter and said pressure transducing means for damping resonant pressure waves, said restrictor means having a passageway therethrough forming a part of said duct, said restrictor means passageway being provided with an orifice in said duct, the restrictor means including adjustable means to adjust the size of said orifice;
    a single pressure transmitting physiological fluid filling said catheter, said duct and said transducing means fluid chamber to transmit the blood pressure variations directly to said fluid chamber without the use of an intermediate fluid, and
    an infusion device for constantly adding sid pressure transmitting fluid to said duct, the infusion device having an infusion passageway forming a part of said duct.

2. The apparatus of claim 1 wherein said adjustable restrictor means is located between said infusion device and said pressure transducing means in said duct.

3. An apparatus for measuring blood pressure comprising:
    an open-ended catheter having a first end adapted to be inserted into a blood vessel;
    pressure transducing means including a fluid chamber, said pressure transducing means being adapted to develop a useful signal responsive to pressure variations in the fluid chamber;
    a duct providing a fluid passageway open between a second end of said catheter and said transducing means fluid chamber;

adjustable restrictor means in series with said catheter and said pressure transducing means for damping resonant pressure waves, said restrictor means having a passageway therethrough forming a part of said duct, said restrictor means passageway being provided with an orifice in said duct, the restrictor means including means to adjust the size of said orifice; and a single pressure transmitting physiological fluid filling said catheter, said duct and said transducing means fluid chamber to transmit the blood pressure variations directly to said fluid chamber without the use of an intermediate fluid.

4. In an apparatus for measuring blood pressure including an open-ended catheter having a first end adapted to be inserted into a blood vessel, pressure transducing means including a fluid chamber, said pressure transducing means being adapted to develop a useful signal responsive to pressure variations in the fluid chamber, a duct providing a fluid passageway open between a second end of said catheter and said transducing means fluid chamber, and a single pressure transmitting physiological fluid filling said catheter, said duct and said transducing means fluid chamber to transmit the blood pressure variations directly to said fluid chamber without the use of an intermediate fluid; the improvement comprising:

adjustable restrictor means in series with said catheter and said pressure transducing means for damping resonant pressure waves, said restrictor means having a passageway therethrough forming a part of said duct, said restrictor means passageway being provided with an orifice in said duct, the restrictor means including means to adjust the size of said orifice.

5. The apparatus of claim 3 or 4 further comprising:
an infusion device for constantly adding the pressure transmitting physiological fluid to said duct, the infusion device having an infusion passageway forming a part of said duct.

6. The apparatus of claim 5 wherein said adjustable restrictor means is located between said infusion device and said pressure transducing means in said duct.

7. The apparatus of claim 1, 3 or 4 wherein the adjustable restrictor means is a manually-operable valve comprising:
a valve body having a generally direct passage therethrough;
a valve seat in the valve body forming the orifice in the passage;
a threadably-adjustable valve element for infinitely varying the size of the orifice up to a predetermined maximum.

8. The apparatus of claim 7 wherein the valve seat is basin-shaped and the orifice is provided by a flexible deformable O-ring having a central opening therethrough aligned with and forming part of said direct passage through said valve body, said ring being seated in said valve seat, said valve having means to compress the ring into the basin-shaped valve seat, thereby making the orifice smaller.

9. The apparatus of claim 7 wherein the variable restrictor means is a needle valve, having a valve seat shaped like a conical frustrum, and a valve element which is a valve needle having a face which is shaped to cooperate with the valve seat, said valve controlling the size of the flow opening by the conjunction of the valve needle and the valve seat.

10. The apparatus of claim 10 wherein the valve body and valve seat are molded in one piece of plastic.

11. The apparatus of claim 1 further comprising
monitor means operably connected to said transducing means, said monitor means being responsive to said signal for providing a useful output indicative of pressure.

12. The apparatus of claim 1 wherein the pressure transmitting physiological fluid is a physiologic saline solution.

13. For use in restricting flow of a liquid or the movement of pressure waves in a liquid, a variable-restrictor valve comprising:
a valve body having a generally direct passage therethrough with the passges through the inlet and outlet ends being coaxial and aligned with each other;
a valve seat in the valve body shaped like a conical frustrum and forming an orifice in the passage said valve seat extending at an angle to the axis of the inlet and outlet ends;
a threadably-adjustable valve needle coaxial with the valve seat for infinitely varying the size of the orifice up to a predetermined maximum;
the valve needle having a face which is shaped to cooperate with the valve seat, said valve controlling the size of the flow opening by the conjunction of the valve needle and the valve seat.

* * * * *